(12) United States Patent
Lee

(10) Patent No.: US 6,965,097 B2
(45) Date of Patent: Nov. 15, 2005

(54) CONTROL DEVICE FOR AN INFRARED RAY SAUNA FACILITY

(76) Inventor: Seung Woo Lee, 18-tong, 4-ban, 199-1 Sungsan 1-dong, Mapo-ku, Seoul (KR)

( * ) Notice: Subject to any disclaimer, the term of this patent is extended or adjusted under 35 U.S.C. 154(b) by 0 days.

(21) Appl. No.: 10/396,246

(22) Filed: Mar. 26, 2003

(65) Prior Publication Data

US 2004/0188415 A1   Sep. 30, 2004

(51) Int. Cl.$^7$ .......................... A61H 33/06; H05B 1/02
(52) U.S. Cl. ..................... 219/492; 392/416; 4/524
(58) Field of Search .......................... 219/492, 494; 4/524, 526, 525; 392/416, 394, 399, 402–403

(56) References Cited

U.S. PATENT DOCUMENTS

| | | | | |
|---|---|---|---|---|
| 4,446,356 | A | * | 5/1984 | Rimmi ........................ 392/386 |
| 4,681,255 | A | * | 7/1987 | Drost ............................ 4/524 |
| 5,117,481 | A | * | 5/1992 | Sung .......................... 392/416 |
| 5,628,073 | A | * | 5/1997 | Popovich ....................... 4/524 |
| 5,796,076 | A | * | 8/1998 | Azuma ....................... 219/486 |
| 2002/0046422 | A1 | * | 4/2002 | Perett ............................ 4/524 |
| 2003/0156831 | A1 | * | 8/2003 | Schaeffer et al. ........... 392/416 |
| 2004/0184793 | A1 | * | 9/2004 | Schaeffer et al. ........... 392/416 |
| 2004/0188637 | A1 | * | 9/2004 | Lee .......................... 250/495.1 |
| 2004/0240864 | A1 | * | 12/2004 | Lee ............................ 392/416 |

FOREIGN PATENT DOCUMENTS

| | | | |
|---|---|---|---|
| DE | 3239049 | * | 5/1984 |
| DE | 3511435 | * | 10/1986 |
| DE | 3511499 | * | 10/1986 |
| DE | 3920036 | * | 1/1991 |
| DE | 19539348 | * | 11/1996 |
| EP | 300577 | * | 1/1989 |
| GB | 2195530 | * | 4/1988 |
| NL | 1001443 | * | 4/1997 |
| WO | 01/24761 | * | 4/2001 |

* cited by examiner

Primary Examiner—John A. Jeffery
(74) Attorney, Agent, or Firm—Park & Sutton LLP; John K. Park

(57) ABSTRACT

A control device for an infrared ray sauna facility is provided. The sauna facility has a chamber and the chamber has a door and infrared ray generating units, and the control device includes a control circuit, an inside control panel that is connected to the control circuit and is installed inside the chamber, and an outside control panel that is connected to the control circuit and is installed outside the chamber. The control circuit controls the infrared ray generating units to adjust the temperature of the sauna facility. Each of the inside control panel and outside control panel includes a display device and an input device. The control circuit includes a clock so that a user of the sauna facility can reserve time to use the sauna facility. The control device also includes a temperature sensor so that the control circuit performs feedback control of the temperature.

5 Claims, 4 Drawing Sheets

CONTROL DEVICE FOR AN INFRARED RAY SAUNA FACILITY

BACKGROUND OF THE INVENTION

The present invention relates to a control device for a sauna facility. More particularly, the invention relates to an infrared ray sauna facility that can be conveniently controlled both from inside and outside of the facility by a user of the facility.

The infrared ray is divided into the near infrared ray that has a wavelength from 0.76 to 1.5 micron, the middle infrared ray that has a wavelength from 1.5 to 5.6 micron, and the far infrared ray that has a wavelength from 5.6 to 1000 micron. Among these, the far infrared ray has a characteristic that may penetrate into human skin up to 40 mm, and resonates molecules that form the human cells; thereby the molecules generate heat by themselves.

An infrared ray sauna facility uses the far infrared ray as its heat source.

In contrast with a typical sauna device that heats air above 100 degree Celsius, the infrared ray sauna facility makes it possible to enjoy sauna at temperature as low as 40~80 degree Celsius. Thus people who cannot enjoy the conventional high temperature sauna, including the old, the weak and children can enjoy sauna safely with the infrared sauna facility.

An infrared ray sauna facility includes a chamber into which a user can enter and sit. The chamber has a door to get into, and a seat for a user. A plurality of infrared ray generating units are installed on the inside wall of the chamber. A controller for controlling the infrared ray generating units is installed outside the chamber. The user controls the temperature inside the chamber or the operating time of the facility with the controller.

With such an infrared ray sauna facility by prior art, when the user wants to change the conditions inside the chamber, such as temperature, the user must open the door and come out of the chamber to access the controller. The user then goes into the chamber again. A disadvantage is that cold outside air flows into the chamber while the door is open, thereby dropping the temperature inside the chamber. It takes some time to return to the adequate temperature, especially when the ambient temperature is low. Also, electric power consumption is increased to compensate the lost heat, and the sauna effect that the user feels diminishes.

SUMMARY OF THE INVENTION

The present invention contrives to solve the disadvantages of the prior art.

Therefore, an object of the invention is to provide an infrared ray sauna facility that can be controlled inside a chamber of the facility.

Another object of the invention is to provide an infrared ray sauna facility that can be controlled both from inside and outside of a chamber of the facility.

To achieve the above-described objects, the invention provides a control device for an infrared ray sauna facility. The sauna facility has a chamber and the chamber has a door and a plurality of infrared ray generating units, and the control device includes a control circuit, an inside control panel that is connected to the control circuit and is installed inside the chamber, and an outside control panel that is connected to the control circuit and is installed outside the chamber. The control circuit controls the infrared ray generating units for controlling temperature inside the chamber.

Each of the inside control panel and outside control panel includes a display device and an input device.

Alternatively, the control device may be constructed without the outside control panel since accessibility inside the chamber of the sauna facility is more essential.

The control circuit includes a clock. When the input device inputs a time period to the clock, the control circuit activates the infrared ray generating units during the time period. In this way, a user of the sauna facility can reserve the time period to use the sauna facility.

The control device also includes a temperature sensor that is installed inside the chamber. The control circuit performs feedback control of the temperature inside the chamber with the temperature sensed by the temperature sensor.

The display device includes a digital display and a window, so that the user can see the digital display through the window.

The advantages of the present invention are: (1) a user of the sauna facility can easily access the control device without getting out of the facility; and (2) temperature and operation time of the sauna device can be controlled both from inside and outside of the chamber.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION OF THE PREFERRED EMBODIMENTS

Figure 1:
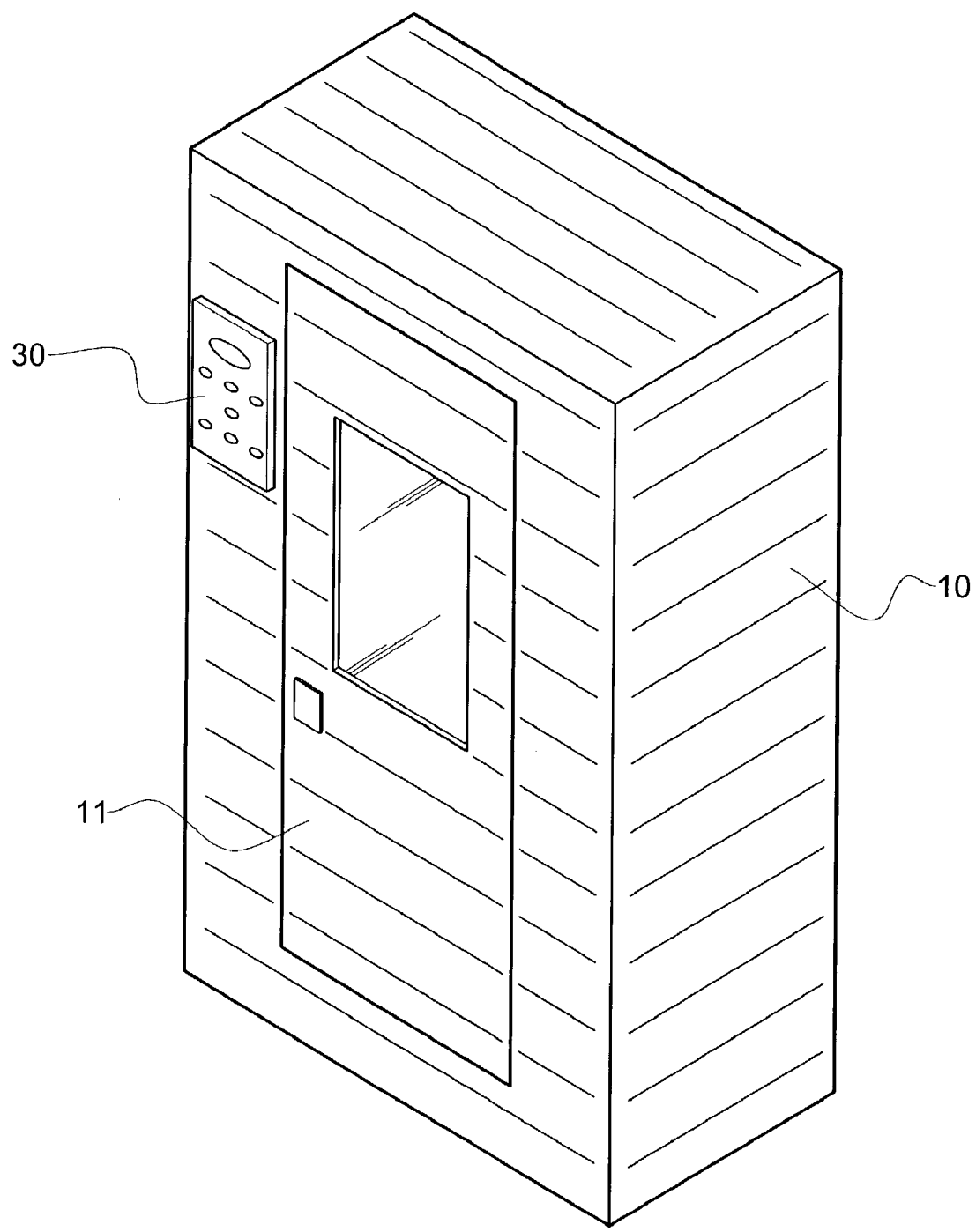
FIG. 1 is a perspective view of an infrared sauna facility according to the present invention.

FIG. 1 shows an infrared sauna facility according to the present invention. The sauna facility has a chamber 10, in which a user enjoys sauna, and the chamber 10 has a door 11 for entry into the chamber 10.

Figure 2:
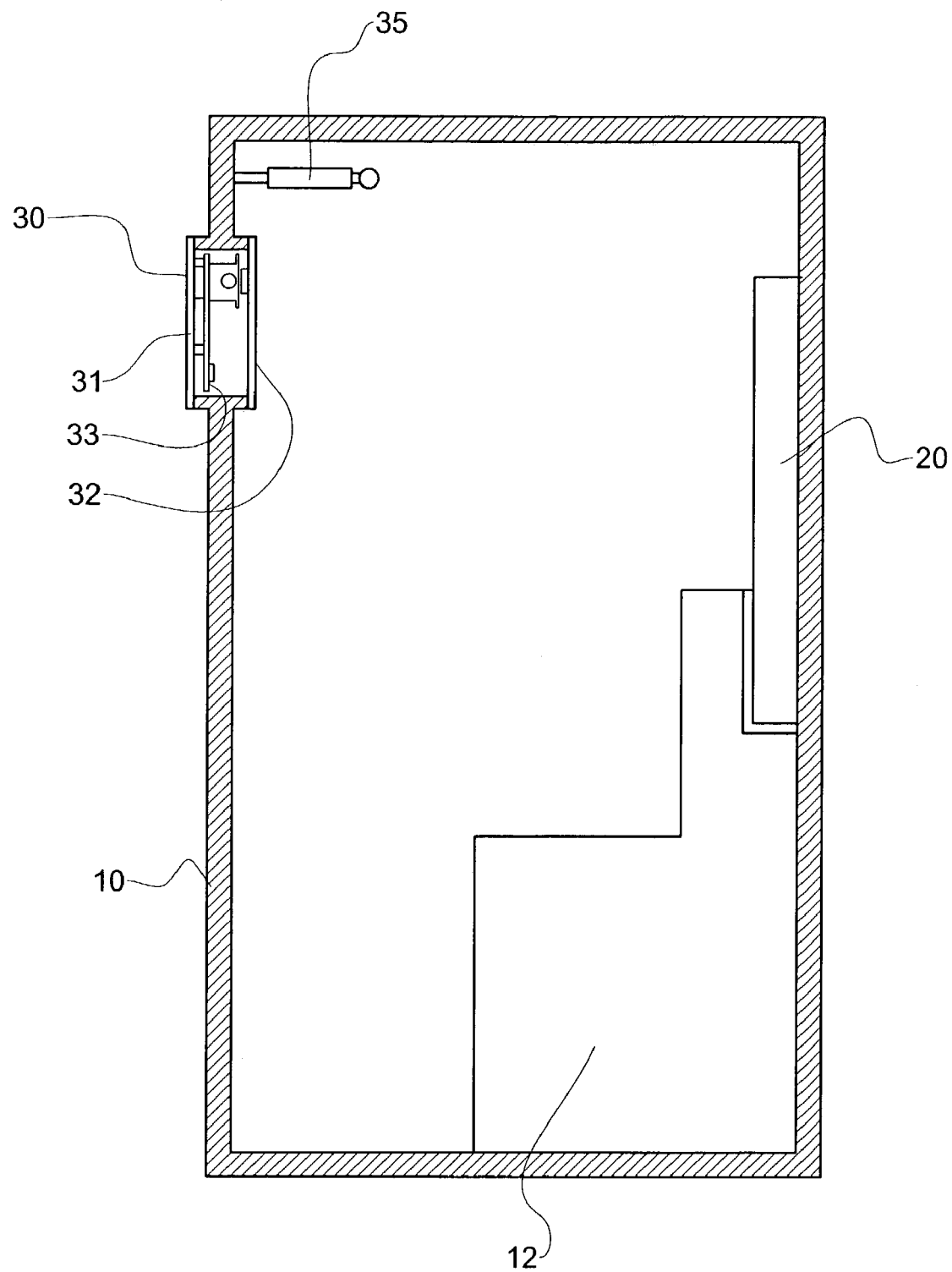
FIG. 2 is a side cross sectional view showing the inside of the sauna facility schematically, and that an inside control panel and an outside control panel face opposite with each other.

FIG. 2 shows a seat 12 provided within the chamber 10 for the user to sit on, a plurality of infrared ray generating units 20 that are installed on the inner wall of the chamber 10 and generate and radiate infrared ray, and a control device 30 for controlling conditions inside the chamber 10.

The chamber 10 is made of wood that absorbs moisture and emanates aroma, or plastic. The infrared ray generating unit 20 includes an infrared ray heater and a reflector that is positioned at the rear of the infrared ray heater. The infrared ray heater includes a heating wire that is received in a ceramic-coated or ceramic-containing pipe. The heating wire generates heat as it is powered with electricity, and the pipe is heated by the heat generated by the heating wire, and radiates infrared rays, preferably far infrared rays. The reflector reflect the infrared rays toward the direction of the user sitting on the seat 12.

The control device 30 includes a control circuit or a main PCB 33, an inside control panel 32 that is connected to the control circuit 33 and is installed inside the chamber 10, and an outside control panel 31 that is connected to the control circuit and is installed outside the chamber 10. The control circuit 33 is positioned between the inside control panel 32 and the outside control panel 31. The control circuit 33 controls the infrared ray generating units 20 for controlling temperature inside the chamber.

Figure 3:
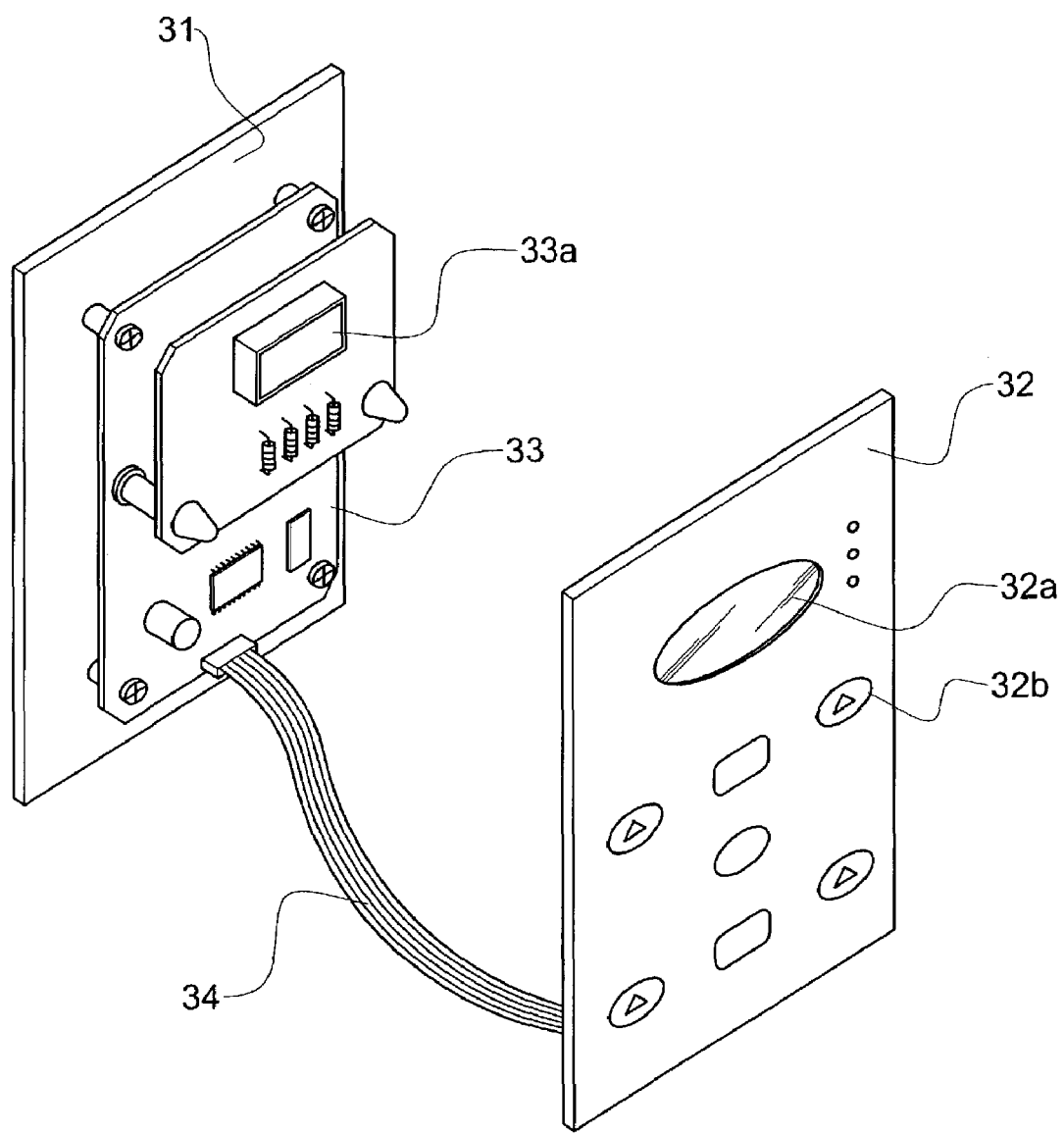
FIG. 3 is a perspective view of a control device for the sauna facility.

FIG. 3 shows the control circuit 33, the outside control panel 31 and the inside control panel 32. The inside control panel 32 is installed inside the chamber 10, and is operationally connected to the control circuit 33 through a cable 34 so that the user can control the infrared ray generating units 20 with the inside control panel 32. Each of the inside control panel 32 and outside control panel 31 includes a display device and an input device. The inside control panel 32 has a window 32a as the display device, and control buttons 32b as the input device. The control circuit 33 has two digital displays 33a and electronic components to control the infrared ray generating units 20. The digital displays 33a are installed between the control circuit 33 and the inside/outside control panels 32, 31. The digital display 33a displays operational status such as temperature and time, etc. The user can see the display through the window 32a. The outside control panel 31 has a similar construction as the inside control panel 32.

The control circuit 33 is controlled by either of the inside/outside control panels 32, 31. The user may set the conditions of the sauna facility, including the temperature and operation time, with the outside control panel 31 before using the sauna facility, and then set the conditions with the inside control panel 32 during using the sauna facility.

Referring back to FIG. 2, a temperature sensor 35 is installed inside the chamber 10. The control circuit 33 performs feedback control of the temperature inside the chamber 10 with the temperature sensed by the temperature sensor 35.

In FIGS. 1 and 2, the outside control panel 31 and the inside control panel 32 face with each other, and are positioned at the same location near the door 11. The control circuit 33 is interposed between the outside control panel 31 and the inside control panel 32.

Figure 4:
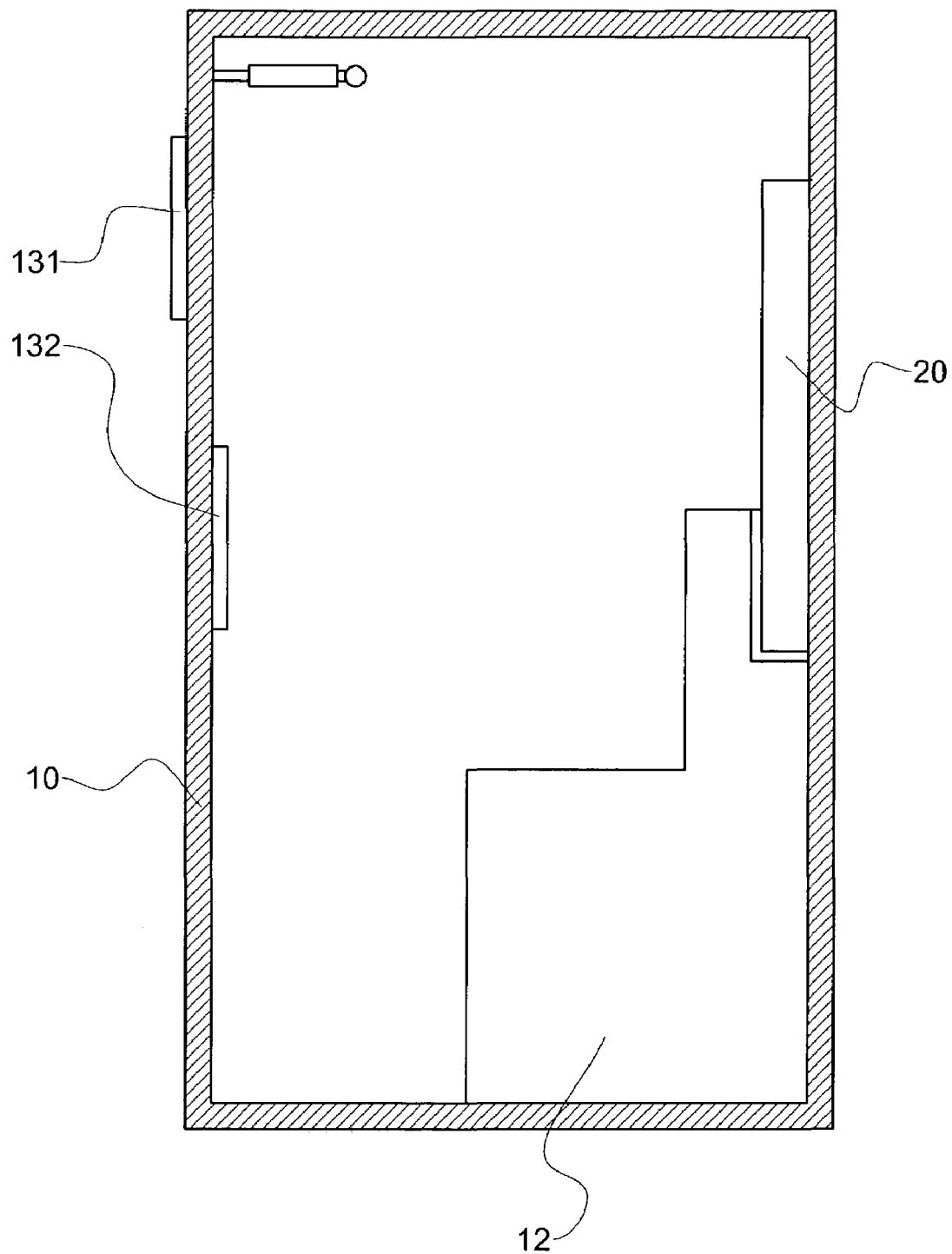
FIG. 4 is a side cross-sectional view showing the inside of the sauna facility schematically, and that an inside control panel and an outside control panel are separately positioned from each other.

FIG. 4 shows a different arrangement of the control panels. An outside control panel 131 is installed outside the chamber 10, and an inside control panel 132 is installed inside the chamber 10. The outside control panel 131 and the inside control panel 132 do not face with each other, but is spaced from each other vertically. Each of the outside/inside control panel 131, 132 has a similar, independent construction and can control the infrared ray generating units 20.

The infrared sauna facility also has a user-programmable sauna session reservation mode. The control circuit 33 includes a 12 hr, AM/PM mode clock (not shown) pre-installed and settable by the user. The user sets the time that he or she would like to use the sauna facility and this time is reserved. The sauna turns on automatically at the user's set time. The user uses the input device of the control panels, to input a time period to the clock. The control circuit 33 activates the infrared ray generating units 20 during the time period.

With the above construction, the user can control the operation time and temperature from either outside and inside of the sauna facility, thereby eliminating the inconvenience of interrupting sauna and unpleasant fluctuation of temperature in the sauna chamber. Also the electric energy is saved.

Although the invention has been described in considerable detail, other versions are possible by converting the aforementioned construction. Therefore, the scope of the invention shall not be limited by the specification specified above.

What is claimed is:

1. A control device for a sauna facility, wherein the sauna facility has a chamber and the chamber has a door and a plurality of infrared ray generating units, the control device comprising:
   a) a control circuit,
   b) an inside control panel that is connected to the control circuit and is installed inside the chamber, and
   c) an outside control panel that is connected to the control circuit and is installed outside the chamber, wherein the control circuit controls the infrared ray generating units for controlling temperature inside the chamber, wherein each of the inside control panel and outside control panel includes a display device and an input device.

2. The control device of claim 1, wherein the control circuit includes a clock, wherein the input device inputs a time period to the clock, and wherein the control circuit activates the infrared ray generating units during the time period, whereby a user of the sauna facility can reserve the time period to use the sauna facility.

3. The control device of claim 1, further comprising a temperature sensor that is installed inside the chamber, wherein the control circuit performs feedback control of the temperature inside the chamber with the temperature sensed by the temperature sensor.

4. The control device of claim 3, wherein the control circuit includes a clock, wherein the input device inputs a time period to the clock, and wherein the control circuit activates the infrared ray generating units during the time period, whereby a user of the sauna facility can reserve the time period to use the sauna facility.

5. The control device of claim 4, wherein the display device includes a digital display and a window, whereby the user can see the digital display through the window.

* * * * *